United States Patent [19]

Gehring et al.

[11] Patent Number: 4,685,957

[45] Date of Patent: Aug. 11, 1987

[54] 1-ARYL-5-IMINOAMINOPYRAZOLES, COMPOSITIONS CONTAINING THEM, AND HERBICIDAL METHOD OF USING THEM

[75] Inventors: Reinhold Gehring, Wuppertal; Otto Schallner, Monheim; Jörg Stetter, Wuppertal; Klaus Lürssen, Bergisch-Gladbach; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 885,064

[22] Filed: Jul. 14, 1986

[30] Foreign Application Priority Data

Aug. 8, 1985 [DE] Fed. Rep. of Germany ....... 3528477

[51] Int. Cl.[4] .................. A01N 43/56; C07D 231/38; C07D 401/04
[52] U.S. Cl. ........................................ 71/92; 546/279; 548/362; 548/376; 548/377
[58] Field of Search ............... 546/279; 548/362, 376, 548/377; 71/92

[56] References Cited

U.S. PATENT DOCUMENTS 4,459,150  7/1984  Hatton et al. .................. 548/362

*Primary Examiner*—Henry R. Jiles
*Assistant Examiner*—Kurt G. Briscoe
*Attorney, Agent, or Firm*—Sprung Horn Kramer & Woods

[57] ABSTRACT

Plant growth regulants and herbicides of the formula

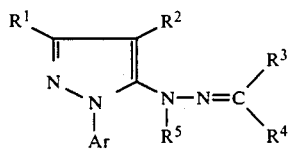

in which
$R^1$ represents hydrogen or alkyl,
$R^2$ represents cyano or nitro,
$R^3$ and $R^4$ independently of one another each represent hydrogen, alkyl, alkoxyalkyl, alkylthioalkyl or halogenoalkyl or represent optionally substituted aryl, or $R^3$ and $R^4$ together represent a divalent alkylene radical,
$R^5$ represents hydrogen or alkyl and
Ar represents optionally substituted phenyl, or represented optionally substituted pyridyl.

8 Claims, No Drawings

1-ARYL-5-IMINOAMINOPYRAZOLES, COMPOSITIONS CONTAINING THEM, AND HERBICIDAL METHOD OF USING THEM

The invention relates to new 1-aryl-pyrazoles, several processes for their preparation and their use as herbicides and plant growth regulators.

It is already known that certain 1-aryl-pyrazoles, such as, for example, 4-cyano-5-propionamido-1-(2,4,6-trichlorophenyl)-pyrazole, have herbicidal properties (compare, for example, DE-OS No. (German Published Specification) 3,226,513).

However, the herbicidal activity of these already known compounds towards harmful plants, like their tolerance towards important crop plants, is not always completely satisfactory in all fields of use.

Nothing is known of an activity as growth regulators in connection with these already known 1-aryl-pyrazoles.

New 1-aryl-pyrazoles of the general formula (I)

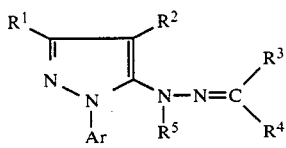

in which
- $R^1$ represents hydrogen or alkyl,
- $R^2$ represents cyano or nitro,
- $R^3$ and $R^4$ independently of one another each represent hydrogen, alkyl, alkoxyalkyl, alkylthioalkyl or halogenoalkyl or represent optionally substituted aryl, or
- $R^3$ and $R^4$ together represent a divalent alkylene radical,
- $R^5$ represents hydrogen or alkyl and
- Ar represents optionally substituted phenyl, or represents optionally substituted pyridyl, have now been found.

It has furthermore been found that the new 1-aryl-pyrazoles of the general formula (I)

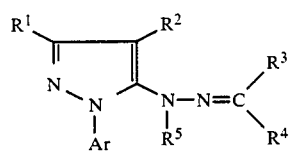

in which
- $R^1$ represents hydrogen or alkyl,
- $R^2$ represents cyano or nitro,
- $R^3$ and $R^4$ independently of one another each represent hydrogen, alkyl, alkoxyalkyl, alkylthioalkyl or halogenoalkyl or represent optionally substituted aryl, or
- $R^3$ and $R^4$ together represent a divalent alkylene radical,
- $R^5$ represents hydrogen or alkyl and
- Ar represents optionally substituted phenyl, or represents optionally substituted pyridyl, are obtained by a process in which
(a) 1-aryl-5-hydrazino-pyrazoles of the formula (II)

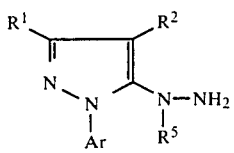

in which
$R^1$, $R^2$, $R^5$ and Ar have the abovementioned meaning, are reacted with aldehydes or ketones of the formula (III)

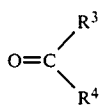

in which
$R^3$ and $R^4$ have the abovementioned meaning, if appropriate in the presence of a diluent, or in which
(b) the 1-aryl-pyrazoles obtainable by process (a) of the formula (Ia)

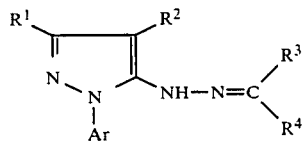

in which
$R^1$, $R^2$, $R^3$, $R^4$ and Ar have the abovementioned meaning,
are reacted with alkylating agents of the formula (IV)

$$R^{5-1}-A \qquad (IV)$$

in which
$R^{5-1}$ represents alkyl and
A represents an electron-attracting leaving group,
if appropriate in the presence of a diluent and if appropriate in the presence of an acid-binding agent or basic catalyst.

Finally, it has been found that the new 1-aryl-pyrazoles of the formula (I) have herbicidal properties, and in particular also selective herbicidal properties, and moreover also have plant growth regulating properties.

Surprisingly, the 1-aryl-pyrazoles of the general formula (I) according to the invention show a considerably improved tolerance towards important crop plants, coupled with a comparably good herbicidal activity against important problem weeds, than the 1-aryl-pyrazoles known from the prior art, such as, for example, 4-cyano-5-propionamido-1-(2,4,6-trichlorophenyl)-pyrazole, which are closely related compounds chemically and from the point of view of their action, and, moreover, entirely unexpectedly, additionally show a plant growth regulatory activity.

Formula (I) provides a general definition of the 1-aryl-pyrazoles according to the invention. Preferred compounds of the formula (I) are those in which
- $R^1$ represents hydrogen, or represents straight-chain or branched alkyl with 1 to 4 carbon atoms,
- $R^2$ represents cyano or nitro,
- $R^3$ and $R^4$ independently of one another each represent hydrogen, or represent in each case straight-chain or branched alkyl, alkoxyalkyl, alkylthiolkyl or halogenoalkyl with in each case 1 to 4 carbon atoms in the individual alkyl parts and, in the case of halogenoalkyl, with 1 to 9 identical or different halogen atoms, or represent phenyl which is optionally monosubstituted or polysubstituted by identical or different substituents, possible substituents in each case being: halogen, cyano, nitro and in each case straight-chain or branched alkyl, alkoxy, alkylthio and halogenoalkyl with in each case 1 to 4 carbon atoms and, in the case of the halogenoalkyl, with 1 to 9 identical or different halogen atoms, or $R^3$ and $R^4$ together represent a straight-chain or branched divalent alkylene radical with 3 to 12 carbon atoms, $R^5$ represents hydrogen, or represents straight-chain or branched alkyl with 1 to 4 carbon atoms and Ar represents phenyl, 2-pyridyl, 3-pyridyl or 4-pyridyl, in each case optionally monosubstituted or polysubstituted by identical or different substituents, possible substituents in each case being: cyano, nitro, halogen, in each case straight-chain or branched alkyl, alkoxy and alkoxycarbonyl with in each case 1 to 4 carbon atoms in the alkyl part, and in addition in each case straight-chain or branched halogenoalkyl and halogenoalkoxy with in each case 1 to 4 carbon atoms and 1 to 9 identical or different halogen atoms, and a radical $-S(O)_m-R^6$ wherein $R^6$ represents amino, or represents in each case straight-chain or branched alkyl, alkylamino, dialkylamino or halogenoalkyl, with each case 1 to 4 carbon atoms in the individual alkyl parts and, in the case of halogenoalkyl, with 1 to 9 identical or different halogen atoms and m represents the number 0, 1 or 2.

Particularly preferred 1-aryl-pyrazoles of the formula (I) are those in which $R^1$ represents hydrogen, methyl, ethyl, n- or i-propyl, or n-, i-, s- or t-butyl, $R^2$ represents cyano or nitro, $R^3$ and $R^4$ independently of one another each represent hydrogen, methyl, ethyl, n- or i-propyl, n-, i-, s- or t-butyl, methoxymethyl, methylthiomethyl, chloromethyl, dichloromethyl, trichloromethyl, trifluoromethyl, chloroethyl, bromoethyl, trichloroethyl or trifluoroethyl, or represent phenyl which is optionally mono-, di- or trisubstituted by identical or different substituents, possible substituents in each case being: fluorine, chlorine, bromine, cyano, nitro, methyl, ethyl, methoxy, methylthio and trifluoromethyl, or $R^3$ and $R^4$ together represent a straight-chain, divalent alkylene radical with 4 to 7 carbon atoms, $R^5$ represents hydrogen, methyl or ethyl and Ar represents phenyl which is optionally monodi-, tri-, tetra- or pentasubstituted by identical or different substituents, or represents 2-pyridyl or 4-pyridyl, in each case optionally mono-, di-, tri- or tetrasubstituted by identical or different substituents, possible substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical $-S(O)_m-R^6$, wherein $R^6$ represents amino, methylamino, ethylamino, dimethylamino, diethylamino, methyl, ethyl, fluorodichloromethyl, difluoromethyl, tetrafluoroethyl, trifluorochloroethyl or trifluoromethyl and m represents the number 0, 1 or 2.

The following 1-aryl-pyrazoles of the general formula (I) may be mentioned specifically, in addition to the compounds mentioned in the preparation examples:

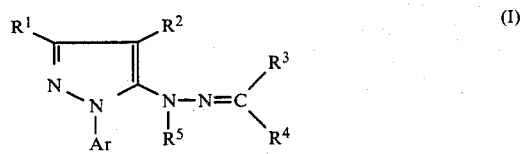

(I)

TABLE 1

| $R^1$ | $R^2$ | $R^3$ | $R^4$ | $R^5$ | Ar |
|---|---|---|---|---|---|
| H | NO$_2$ | CH$_3$ | C$_2$H$_5$ | H | 2,6-Cl$_2$-4-CF$_3$-C$_6$H$_2$ |
| H | NO$_2$ | CH$_3$ | i-C$_3$H$_7$ | H | 2,6-Cl$_2$-4-CF$_3$-C$_6$H$_2$ |
| H | NO$_2$ | CH$_3$ | i-C$_4$H$_9$ | H | 2,6-Cl$_2$-4-CF$_3$-C$_6$H$_2$ |
| H | NO$_2$ | CH$_3$ | C$_6$H$_5$ | H | 2,6-Cl$_2$-4-CF$_3$-C$_6$H$_2$ |
| H | NO$_2$ | CH$_3$ | CH$_3$ | CH$_3$ | 2,6-Cl$_2$-4-CF$_3$-C$_6$H$_2$ |
| H | NO$_2$ | CH$_3$ | CH$_2$—OCH$_3$ | H | 2,6-Cl$_2$-4-CF$_3$-C$_6$H$_2$ |

TABLE 1-continued

| R¹ | R² | R³ | R⁴ | R⁵ | Ar |
|----|----|----|----|----|-----|
| H | NO₂ | CH₃ | CH₂Cl | H | 2,5-Cl₂-4-CF₃-phenyl |
| H | NO₂ | CH₃ | CH₂—SCH₃ | H | 2,5-Cl₂-4-CF₃-phenyl |
| H | NO₂ | CH₃ | CH₃ | H | 2-Cl-4-CF₃-phenyl |
| H | CN | CH₃ | C₂H₅ | H | 2-Cl-4-CF₃-phenyl |
| H | CN | CH₃ | i-C₃H₇ | H | 2-Cl-4-CF₃-phenyl |
| H | CN | CH₃ | i-C₄H₉ | H | 2-Cl-4-CF₃-phenyl |
| H | CN | CH₃ | phenyl | H | 2-Cl-4-CF₃-phenyl |
| H | CN | CH₃ | CH₂—OCH₃ | H | 2-Cl-4-CF₃-phenyl |
| H | CN | CH₃ | CH₂Cl | H | 2-Cl-4-CF₃-phenyl |
| H | CN | CH₃ | CH₂—SCH₃ | H | 2-Cl-4-CF₃-phenyl |
| H | CN | CH₃ | phenyl | H | 2-Cl-4-OCF₃-phenyl |
| H | CN | H | phenyl | H | 2-Cl-4-OCF₃-phenyl |

If, for example, 4-cyano-5-hydrazino-1-(2,4-dichlorophenyl)-pyrazole and acetone are used as starting substances, the course of the reaction in process (a) according to the invention can be represented by the following equation:

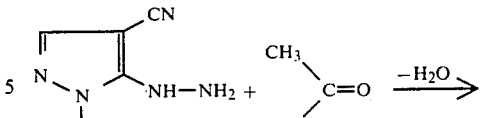

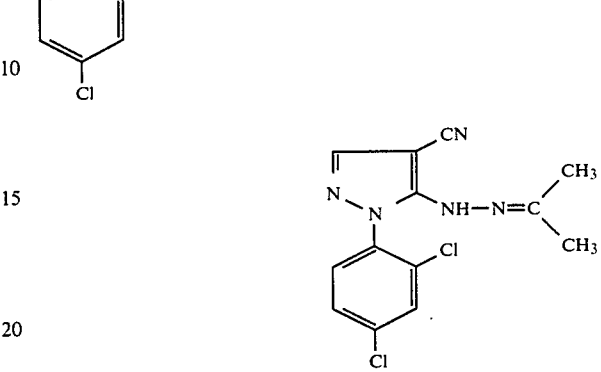

If, for example, 4-cyano-5-(2-propylideneimino)amino-1-(2,6-dichloro-4-trifluoromethyl-phenyl)-pyrazole and methyl iodide are used as starting substances, the course of the reaction in process (b) according to the invention can be represented by the following equation:

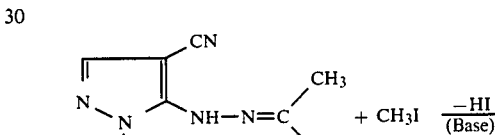

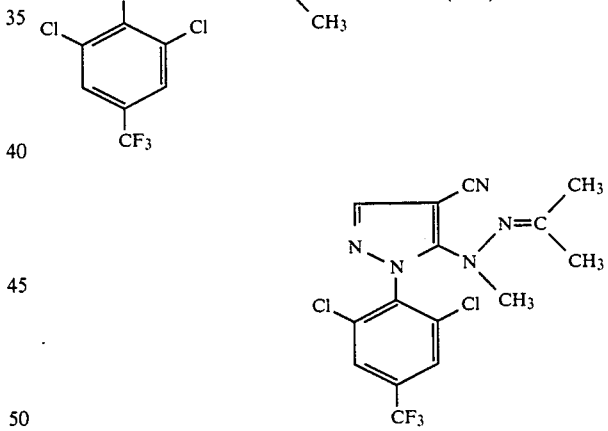

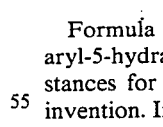

Formula (II) provides a general definition of the 1-aryl-5-hydrazino-pyrazoles required as starting substances for carrying out process (a) according to the invention. In this formula (II), R¹, R², R⁵ and Ar preferably represent those radicals which have already been mentioned as preferred for these substituents in connection with the description of the substances of the formula (I) according to the invention.

The 1-aryl-5-hydrazino-pyrazoles of the formula (II) are known in some cases (compare, for example, J. Heterocycl. Chem. 20, 277-279 (1983), and some of them are the subject of commonly assigned German application Ser. No. 35 28 478, filed Aug. 8, 1985, now pending. They are obtained, for example, by a process in which 1-aryl-5-halogenopyrazoles of the formula (V)

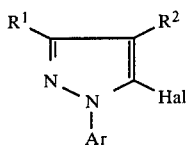

(V)

in which

R¹, R² and Ar have the abovementioned meaning and Hal represents halogen, are reacted with hydrazine derivatives of the formula (VI)

(VI)

in which

R⁵ has the abovementioned meaning, if appropriate in the presence of a diluent, such as, for example, dioxane, at temperatures between 20° C. and 150° C.

The 1-aryl-5-halogeno-pyrazoles of the formula (V) are the subject of commonly assigned application Ser. No. 816,643, filed Jan. 6, 1986, now pending (corresponding to German Pat. No. 3,501,323 of Jan. 17, 1985) and German Pat. No. 3,520,329 of June 7, 1985.

They are obtained, for example, by a process in which 5-amino-1-aryl-pyrazoles of the formula (VII)

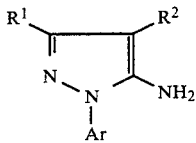

(VII)

in which

R¹, R² and Ar have the abovementioned meaning, are diazotized with nitrite compounds of the formula (VIII)

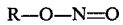

(VIII)

in which

R represents hydrogen or alkyl, or represents an alkali metal cation, in the customary manner in the presence of a hydrogen halide acid, such as, for example, hydrochloric acid or hydrobromic acid, or in the presence of a haloform, such as, for example, chloroform or bromoform, at temperatures between −20 ° C. and +80° C. (compare, for example, "Organikum" 15th edition VEB Deutscher Verlag der Wissenschaften, Berlin 1981, page 652 et seq; J. Chem. Soc. C, 1966, 1249 or Rev. Latinoam. Quim. 13, 100–102 [1982]).

The 5-amino-1-aryl-pyrazoles of the formula (VII) are known in some cases (compare, for example, European Pat. No. 26,034, European Pat. No. 53,678 or European Pat. No. 34,945 and DE-OS No. (German Published Specification) 3,226,496, DE-OS No. (German Published Specification) 3,408,727 or DE-OS No. (German Published Specification) 3,420,985), and some of them are the subject of application Ser. No. 690,347, filed Jan. 10, 1985, now pending, (corresponding to German Pat. No. 3,402,308 of Jan. 24, 1984) German Pat. Nos. 3,520,330 of June 7, 1985 and 3,520,327 of June 7, 1985.

They are obtained, for example, by a process in which aryl-hydrazines of the formula (IX)

Ar—NH—NH₂ (IX)

in which

Ar has the abovementioned meaning, are either initially reacted in a 1st stage (α) with acrylonitrile derivatives of the formula (X)

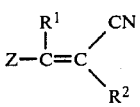

(X)

in which

R¹ and R² have the abovementioned meaning and z represents halogen, hydroxyl, alkoxy or dialkylamino, or (β) with 2-halogenoacrylonitriles of the formula (XI)

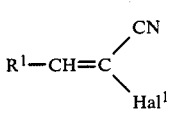

(XI)

in which

R¹ has the abovementioned meaning and

Hal¹ represents halogen, in particular chlorine or bromine, if appropriate in the presence of a diluent, such as, for example, glacial acetic acid or ethanol, and if appropriate in the presence of a reaction auxiliary, such as, for example, sodium acetate, at temperatures between −20 ° C. and +20° C., to give the arylhydrazine derivatives of the formula (XII)

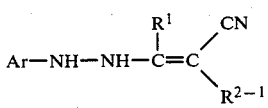

(XII)

in which

Ar has the abovementioned meaning and

R²⁻¹ represents halogen, cyano or nitro, and these are cyclized in a 2nd stage, if appropriate in the presence of a diluent, such as, for example, ethylene glycol monoethyl ether, and if appropriate in the presence of an acid catalyst, such as, for example, sulphuric acid or phosphoric acid, at temperatures between +50° C. and +150° C., or are cyclized directly in one reaction step, without isolation of the intermediate stage of the formula (XII), if appropriate in the presence of a diluent, for example ethylene glycol monoethyl ether or ethanol, at temperatures between +50° C. and +150° C., and, if appropriate, the 5-amino-pyrazoles which are unsubstituted in the 4-position and are obtainable by variant (β), of the formula (XIII)

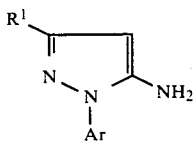 (XIII)

in which
R¹ and Ar have the abovementioned meanings, are hydrated in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C.

If appropriate, it can then be of advantage to protect the amino group in the 5-position of the pyrazole ring with the aid of customary protective group techniques, for example by acylation, before the nitration reaction and, when the nitration has been carried out, to split off the amino-protective group again, likewise in the customary manner, for example by hydrolysis with an aqueous or alcoholic base.

The arylhydrazines of the formula (IX) are known (compare, for example, U.S. Pat. No. 4,127,575; U.S. Pat. No. 3,609,158; DE-OS No. (German Published Specification) 2,558,399; and J. Chem. Soc. C, 1971, 167–174), or they can be obtained by known processes in a simple analogous manner (compare, for example, Houben-Weyl "Methoden der organischen Chemie" ("Methods of Organic Chemistry"), Volume X/2, page 203, Thieme Verlag Stuttgart, 1967), for example by a procedure in which the known anilines or pyridylamines of the formula (XIV)

Ar—NH₂ (XIV)

in which
Ar has the abovementioned meaning,
are reacted with sodium nitrite in the presence of an acid, such as, for example, sulphuric acid, and the products are then reacted with tin-II chloride, likewise in the presence of an acid, such as, for example, hydrochloric acid, at temperatures between −20° C. and +80° C., or in which halogenoaromatics of the formula (XV)

Ar—Hal² (XV)

in which
Ar has the abovementioned meaning and
Hal² represents halogen, in particular fluorine, chlorine or bromine,
are reacted with hydrazine hydrate, if appropriate in the presence of a diluent, such as, for example, pyridine or dioxane, at temperatures between 0° and 150° C.

The hydrazine derivatives of the formula (VI), the nitrite compounds of the formula (VIII), the acrylonitrile derivatives of the formula (X), the 2-halogenoacrylonitriles of the formula (XI), the anilines and pyridylamines of the formula (XIV) and the halogenoaromatics of the formula (XV) are generally known compounds of organic chemistry.

Formula (III) provides a general definition of the aldehydes and ketones furthermore required as starting substances for carrying out process (a) according to the invention. In this formula (III), R³ and R⁴ preferably represent those radicals which have already been mentioned as preferred for these substituents in connection with the description of the substances of the formula (I) according to the invention.

The aldehydes and ketones of the formula (III) are generally known compounds of organic chemistry.

Formula (Ia) provides a general definition of the 1-aryl-pyrazoles required as starting substances for carrying out process (b) according to the invention. In this formula (Ia), R¹, R², R³, R⁴ and Ar preferably represent those radicals which have already been mentioned as preferred for these substituents in connection with the description of the substances of the formula (I) according to the invention.

The 1-aryl-pyrazoles of the formula (Ia) are compounds according to the invention and are obtainable with the aid of process (a) according to the invention.

Formula (IV) provides a general definition of the alkylating agents furthermore required as starting substances for carrying out process (b) according to the invention. In this formula (IV), R⁵⁻¹ preferably represents straight-chain or branched alkyl with 1 to 4 carbon atoms, in particular methyl or ethyl. A preferably represents chlorine, bromine or iodine, or represents p-toluenesulphonyloxy or methoxysulphonyloxy.

The alkylating agents of the formula (IV) are generally known compounds of organic chemistry.

Possible diluents for carrying out process (a) according to the invention are inert organic diluents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylpyrrolidone or hexamethylphosphoric acid triamide, or esters, such as ethyl acetate.

If ketones or aldehydes of the formula (III) in liquid form are used as reaction partners, these can particularly preferably be simultaneously used as the diluent, in a corresponding excess.

The reaction temperatures can be varied within a substantial range in carrying out process (a) according to the invention. The reaction is in general carried out at temperatures between 20° C. and 150° C., preferably at temperatures between 30° C. and 100° C.

For carrying out process (a) according to the invention, in general 1.0 to 30.0 moles, preferably 1.0 to 10.0 moles, of ketone or aldehyde of the formula (III) are employed per mole of 1-aryl-5-hydrazino-pyrazole of the formula (II). The reaction is carried out and the reaction products of the formula (I) are worked up and isolated by generally customary methods.

Possible diluents for carrying out process (b) according to the invention are likewise inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, nitriles, such as acetonitrile or propionitrile, amides, such as dimethylformamide, dimethylacetamide, N-methylformanilide, N-methylprrolidone or hexamethylphosphoric acid triamide, or esters, such as ethyl acetate.

If appropriate, process (b) according to the invention is carried out in the presence of a base which acts as a catalyst and/or acid-binding agent.

Possible such bases are all the customary inorganic or organic bases. These include, for example, alkali metal hydroxides, hydrides or alcoholates, such as sodium hydroxide or potassium hydroxide, sodium hydride or sodium methylate or potassium t-butylate, alkali metal carbonates, such as sodium carbonate, potassium carbonate or sodium bicarbonate, and tertiary amines, such as triethylamine N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a substantial range in carrying out process (b) according to the invention. The reaction is in general carried out at temperatures between $-20°$ C. and $+120°$ C., preferably at temperatures between $0°$ C. and $100°$ C.

For carrying out process (b) according to the invention, in general 1.0 to 30.0 moles, preferably 1.0 to 15.0 moles, of alkylating agent of the formula (IV) and, if appropriate, 0.1 to 5.0 moles, preferably 0.5 to 1.5 moles, of base are employed per mole of 1-arylpyrazole of the formula (Ia). The reaction is carried out and the reaction products of the formula (I) are worked up and isolated by customary processes.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating monocotyledon and dicotyledon weeds, preferably in monocotyledon crops, such as, for example, wheat.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants in undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constitutents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the forces required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Refarding the shooting of buds or the germination of seeds with the aid of growth regulators can be desirable in regions where frost is a hazard, in order to avoid damage by late frosts.

Finally, resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, wettable powders, suspensions, powders, dusting agents, pastes, soluble powders, aerosols, granules, suspension-emulsion concentrates, natural and synthetic materials impregnated with active compound, very fine capsules in polymeric substances and in coating compositions for use on seed, as well as ULV formulations.

These formulations are produced in known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea, for combating weeds in cereals; 4-amino-3-methyl-6-phenyl-1,2,4-triazin5(4H)-one for combating weeds in sugar beet and 4-amino-6-(1,1-dimethylethyl)-3-methylthio-1,2,4-triazin-5(4H)-one for combating weeds in soy beans.

Mixtures with N,N-dimethyl-N'-(3-trifluoromethyl-phenyl)-urea; N,N-dimethyl-N'-(3-chloro-4-methyl-phenyl)-urea; N,N-dimethyl-N'-(4-isopropylphenyl)-urea; 4-amino-6-t-butyl-3-ethylthio-1,2,4-triazin-5-(4H)-one; 2,4-dichlorophenoxyacetic acid; 2,4-dichlorophenoxy-propionic acid; (2-methyl-4-chlorophenoxy)-acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; 2-benzyloxyethyl, trimethylsilyl-methyl or 2,2-diethoxyethyl 2-[4-(3,5-dichloropyrid-2-yloxy)-phenoxy]-propionate; 2-[1-(ethoxyamino)-butylidene]-5-(2-ethylthiopropyl)-1,3-cylcohexanedione; methyl 5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; 4-ethylamino-2-t-butylamino-6-methylthio-s-triazine; 2-{4-[<3-chloro-5-(trifluoromethyl)-2-pyridyl>-oxy]-phenoxy{-propanoic acid or propanoic acid ethyl ester; 5-(2-chloro-4-trifluoromethylphenoxy)-2-nitrobenzoic acid; N-(1-ethylpropyl)-3,4-dimethyl-2,6-dinitroaniline; N-methyl-2-(1,3-benzothiazol-2-yloxy)-acetanilide; S-(2,3,3-trichloroallyl) N,N-diisopropyl-thiolcarbamate; and 2-[5-methyl-(1-methylethyl)-4-oxo-2-imidazolin-2-yl]-3-quinolinecarboxylic acid, where appropriate, are also of advantage. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergency of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Futhermore, it is possible to apply the active compounds in accordance with the ultra-low volume process or to inject the active compound preparation or the active compound itself into the soil. It is also possible to treat the seeds of plants.

When used as plant growth regulators, the amounts applied can likewise be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

When applied in appropriate amounts, the active compounds according to the invention moreover also exhibit an activity as leaf insecticides.

The preparation and use of the active compounds according to the invention can be seen from the following examples:

PREPARATION EXAMPLES

EXAMPLE 1

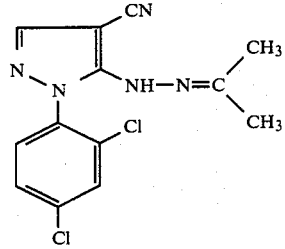

3 g (0.011 mole) of 4-cyano-5-hydrazino-1-(2,4-dichlorophenyl)-pyrazole are warmed at the boiling point in 30 ml of acetone for 2 minutes. The acetone is distilled off and the crystalline residue is recrystallized from toluene.

2.7 g (78% of theory) of 5-[N-(2-propylideneimino)-amino]-4-cyano-1-(2,4-dichlorophenyl)-pyrazole of melting point 175° C. are obtained.

Preparation of the starting compounds

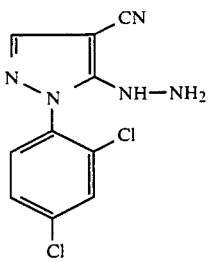

6.4 g (0.02 mole) of 5-bromo-4-cyano-1,(2,4-dichlorophenyl)-pyrazole and 15 g (0.2 mole) of hydrazine hydrate in 80 ml of dioxane are stirred at the reflux temperature for 20 hours, the mixture is then concentrated under reduced pressure and the residue is stirred with water, filtered off with suction and recrystallized twice from ethanol.

2.1 g (40% of theory) of 4-cyano-5-hydrazino-1-(2,4-dichlorophenyl)-pyrazole of melting point 199°–204° C. are obtained.

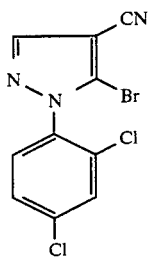

6 g (0.09 mole) of sodium nitrite in 15 ml of water are added to a suspension of 12.7 g (0.05 mole) of 5-amino-4-cyano-1-(2,4-dichlorophenyl)-pyrazole in 100 ml of hydrobromic acid at −5° C. to 0° C. and the mixture is stirred until the evolution of gas has ended, the temperature rising to 30° C. The solid residue is filtered off with suction, suspended in water, neutralized with sodium bicarbonate and filtered off with suction again and dried.

14.5 g (91.5% of theory) of 5-bromo-4-cyano-1-(2,4-dichlorophenyl)-pyrazole of melting point 84° C. (decomposition) are obtained.

EXAMPLE 2

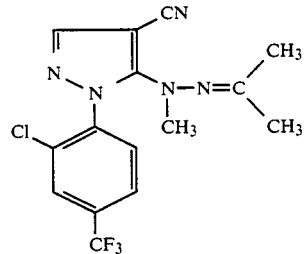

2.3 g (0.007 mole) of 5-(α-methylhydrazino)-4-cyano-1-(2-chloro-4-trifluoromethyl-phenyl)-pyrazole are heated at the boiling point in 20 ml of acetone for 2 minutes. The acetone is distilled off and the oily residue is separated by column chromatography (silica gel/mobile phase: chloroform-acetone 9:1).

2.0 g (76.4% of theory) of 4-cyano-5-[N-methyl-N-(2-propylideneimino)-amino]-1-(2-chloro-4-trifluoromethyl-phenyl)-pyrazole of melting point 162° C. are obtained.

Preparation of the starting compound

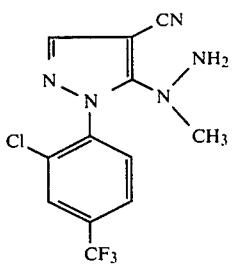

3.5 g (0.01 mole) of 5-bromo-4-cyano-1-(2-chloro-4-trifluoromethyl-phenyl)-pyrazole and 13.8 g (0.3 mole) of N-methyl-hydrazine are heated under reflux in 100 ml of dioxane for 5 days, the mixture is concentrated in vacuo, the residue is taken up in chloroform and the mixture is washed three times with water, dried over sodium sulphate and freed from the solvent in vacuo.

2.3 g (72% of theory) of 5-(α-methylhydrazino)-4-cyano-1-(2-chloro-4-trifluoromethyl-phenyl)-pyrazole are obtained as an oil.

$^1$H-NMR (CDCL$_3$/TMS as the internal standard) δ=3.3 ppm (α-methylhydrazino group)

The following 1-aryl-pyrazoles of the general formula (1) are obtained in a corresponding manner and in accordance with the general statements on the preparation:

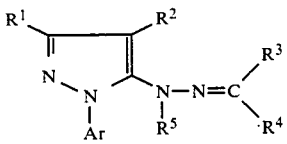

TABLE 2

| Example No. | R$^1$ | R$^2$ | R$^3$ | R$^4$ | R$^5$ | Ar | Melting point °C. |
|---|---|---|---|---|---|---|---|
| 3 | H | NO$_2$ | CH$_3$ | CH$_3$ | H | 2,4,5-Cl$_3$-C$_6$H$_2$ | 130–131 |
| 4 | H | CN | CH$_3$ | CH$_3$ | H | 2-Cl-4-CF$_3$-C$_6$H$_3$ | 134–136 |
| 5 | H | NO$_2$ | CH$_3$ | CH$_3$ | H | 2-Cl-4-CF$_3$-5-Cl-C$_6$H$_2$ | 110–115 |
| 6 | H | NO$_2$ | CH$_3$ | CH$_3$ | H | 2-Cl-4-CF$_3$-5-Br-C$_6$H$_2$ | 94–100 |

USE EXAMPLES

The compound shown below was employed as the comparison substance in the following use examples:

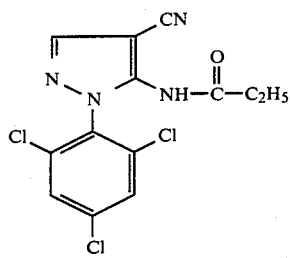

(A)

4-cyano-5-propionamido-1-(2,4,6-trichloro-phenyl)-pyrazole (known from DE-OS No. (German Published Specification) 3,226,513)

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of active compound in such a way as to apply the particular amounts of active compound desired per unit area. The concentration of the spray Liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior selectivity for crop plants compared with the prior art is shown, for example, by the compound according to preparation Example 4.

EXAMPLE B

Growth of barley

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 3 weeks, the additional growth is measured on all plants and is calculated in per cent of the additional growth of the control plants. 100% denotes an additional growth as in the controls, values below 100% represent inhibition of growth and values above 100% represent promotion of growth.

In this test, a clear activity in comparison with the untreated control is shown, for example, by the compound according to preparation Example 1.

EXAMPLE C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:

0 denotes no desiccation of leaves, no shedding of leaves
+ denotes slight desiccation of the leaves, slight shedding of leaves
+ + denotes severe desiccation of the leaves, severe shedding of leaves
+ + + denotes very severe desiccation of the leaves, very severe shedding of leaves.

In this test, a clear activity in comparison with the untreated control is shown, for example, by the compounds according to preparation Examples 1 and 4.

It will be understood that the specification and examples are illustrative but not limitative of the present invention and that other embodiments within the spirit and scope of the invention will suggest themselves to those skilled in the art.

We claim:

1. A 1-aryl-pyrazole of the formula

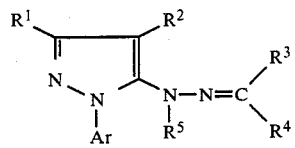

in which
R$^1$ represents hydrogen, or represents straight-chain or branched alkyl with 1 to 4 carbon atoms,
R$^2$ represents cyano or nitro,
R$^3$ and R$^4$ independently of one another each represent hydrogen, or represent in each case straight-chain or branched alkyl, alkoxyalkyl, alkylthioalkyl or halogenoalkyl with in each case 1 to 4 carbon atoms in the individual alkyl parts and, in the case of halogenoalkyl, with 1 to 9 identical or different halogen atoms, or represent phenyl which is optionally monosubstituted or polysubstituted by identical or different substituents selected from the group consisting of halogen, cyano, nitro and in each case straight-chain or branched alkyl, alkoxy, alkylthio and halogenoalkyl with in each case 1 to 4 carbon atoms and, in the case of the halogenoalkyl, with 1 to 9 identical or different halogen atoms, or $R^3$ and $R^4$ together represent a straight-chain or branched divalent alkylene radical with 3 to 12 carbon atoms, $R^5$ represents hydrogen, or represents straight-chain or branched alkyl with 1 to 4 carbon atoms and Ar represents phenyl, 2-pyridyl, 3-pyridyl or 4-pyridyl, in each case optionally monosubstituted or polysubstituted by identical or different substituents selected from the group consisting of cyano, nitro, halogen, in each case straight-chain or branched alkyl, alkoxy and alkoxycarbonyl with in each case 1 to 4 carbon atoms in the alkyl part, and in addition in each case straight-chain or branched halogenoalkyl and halogenoalkoxy with in each case 1 to 4 carbon atoms and 1 to 9 identical or different halogen atoms, and a radical —S(O)$_m$—R$^6$ wherein $R^6$ represents amino, or represents in each case straight-chain or branched alkyl, alkylamino, dialkylamino or halogenoalkyl, with in each case 1 to 4 carbon atoms in the individual alkyl parts and, in the case of halogenoalkyl, with 1 to 9 identical or different halogen atoms and m represents the number 0, 1 or 2.

2. A 1-aryl-pyrazole according to claim 1, in which $R^1$ represents hydrogen, methyl, ethyl, n- or i-propyl, or n-, i-, s- or t-butyl, $R^2$ represents cyano or nitro, $R^3$ and $R^4$ independently of one another each represent hydrogen, methyl, ethyl, n- or i-propyl, n-, i-, s- or t-butyl, methoxymethyl, methylthiomethyl, chloromethyl, dichloromethyl, trichloromethyl, trifluoromethyl, chloroethyl, bromoethyl, trichloroethyl or trifluoroethyl, or represent phenyl which is optionally mono-, di- or trisubstituted by identical or different substituents selected from the group consisting of fluorine, chlorine, bromine, cyano, nitro, methyl, ethyl, methoxy, methylthio and trifluoromethyl, or $R^3$ and $R^4$ together represent a straight-chain, divalent alkylene radical with 4 to 7 carbon atoms, $R^5$ represents hydrogen, methyl or ethyl and Ar represents phenyl which is optionally mono-, di-, tri-, tetra- or pentasubstituted by identical or different substituents, or represents 2-pyridyl or 4-pyridyl, in each case optionally mono-, di-, tri- or tetrasubstituted by identical or different substituents selected from the group consisting of cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)$_m$—R$^6$, wherein $R^6$ represents amino, methylamino, ethylamino, dimethylamino, diethylamino, methyl, ethyl, fluorodichloromethyl, difluoromethyl, tetrafluoroethyl, trifluorochloromethyl, or trifluoromethyl and m represents the number 0, 1 or 2.

3. A 1-aryl-pyrazole according to claim 1, wherein such compound is 5-[N-(2-propylideneimino)-amino]-4-cyano-1-(2,4-dichlorophenyl)-pyrazole of the formula

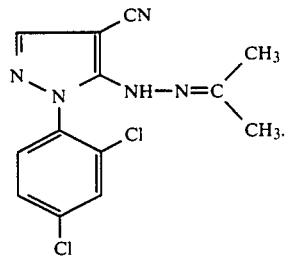

4. A 1-aryl-pyrazole according to claim 1, wherein such compound is 5-[N-(2-propylideneimino)-amino]-4-cyano-1-(2-chloro-4-trifluoromethylphenyl)pyrazole of the formula

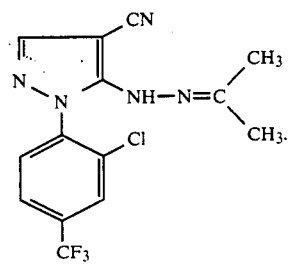

5. A herbicidal or plant growth regulating composition comprising an amount of a compound according to claim 1 effective therefor and a diluent.

6. A method of regulating the growth of plants which comprises applying to such plants or to a locus in which said plants are grown or to be grown, a plant growth regulating effective amount of a compound according to claim 1.

7. The method according to claim 6, wherein the compound is applied in an amount to kill or inhibit the growth of such plant.

8. The method according to claim 6, wherein such compound is

5-[N-(2-propylideneimino)-amino]-4-cyano-1-(2,4-dichlorophenyl)-pyrazole or

5-[N-(2-propylideneimino)-amino]-4-cyano-1-(2-chloro-4-trifluoromethylphenyl)-pyrazole.

* * * * *